United States Patent
Samson et al.

(10) Patent No.: US 11,016,754 B2
(45) Date of Patent: May 25, 2021

(54) INFUSION PUMPS WITH RFID USER IDENTIFICATION

(71) Applicant: Elatec GmbH, Puchheim (DE)

(72) Inventors: Dominik Samson, Taufkirchen (DE); Stefan Haertel, Puchheim (DE)

(73) Assignee: ELATEC GmbH

(*) Notice: Subject to any disclaimer, the term of this patent is extended or adjusted under 35 U.S.C. 154(b) by 147 days.

(21) Appl. No.: 16/233,739

(22) Filed: Dec. 27, 2018

(65) Prior Publication Data
US 2019/0205578 A1    Jul. 4, 2019

(51) Int. Cl.
| | |
|---|---|
| *G06F 8/654* | (2018.01) |
| *G06F 8/65* | (2018.01) |
| *H04W 4/80* | (2018.01) |
| *G06F 21/57* | (2013.01) |
| *H04L 29/08* | (2006.01) |
| *G16H 20/17* | (2018.01) |
| *G16H 40/63* | (2018.01) |
| *G06K 7/10* | (2006.01) |

(52) U.S. Cl.
CPC ............ *G06F 8/654* (2018.02); *G06F 8/65* (2013.01); *G06F 21/572* (2013.01); *G06K 7/10366* (2013.01); *G16H 20/17* (2018.01); *G16H 40/63* (2018.01); *H04L 67/26* (2013.01); *H04W 4/80* (2018.02)

(58) Field of Classification Search
CPC .... G06F 19/3468; G16H 20/17; A61M 5/172; A61M 5/14; A61M 5/142; G06K 7/10366
See application file for complete search history.

(56) References Cited

U.S. PATENT DOCUMENTS

| | | | |
|---|---|---|---|
| 7,743,975 B2 | 6/2010 | Miller | |
| 9,948,758 B1* | 4/2018 | Choi | H04M 1/56 |
| 2003/0135388 A1* | 7/2003 | Martucci | G06Q 10/087 705/2 |
| 2004/0167804 A1* | 8/2004 | Simpson | A61B 5/4839 705/3 |
| 2013/0317753 A1* | 11/2013 | Kamen | G16H 40/20 702/19 |
| 2016/0228633 A1 | 8/2016 | Welsch et al. | |
| 2020/0193806 A1* | 6/2020 | Finke | A61M 15/0018 |

FOREIGN PATENT DOCUMENTS

WO    2009124134 A2    10/2009

* cited by examiner

*Primary Examiner* — Suezu Ellis
(74) *Attorney, Agent, or Firm* — Yakov Sidorin; Quarles & Brady LLP

(57) ABSTRACT

An infusion pump system including an RFID reader and an infusion pump device, the latter containing a controller, a communication interface, and a fluidic pump. The RFID reader includes a microcontroller, a memory storage, an RFID reader communication device, and an RFID manager that is configured to read a user identification parameter from the RFID reader communication device. The RFID reader communication device is configured to communicate with an access unit connected to a network, to query user-related information based on the user identification from a server over the network and to communicate with the communication interface of the infusion pump to forward the user related information to the infusion pump device.

11 Claims, 3 Drawing Sheets

INFUSION PUMPS WITH RFID USER IDENTIFICATION

CROSS-REFERENCE TO RELATED APPLICATIONS

This application claims priority from the pending German Application No. DE 10 2017 223 857.7 filed on 28 Dec. 2017, the disclosure of which is incorporated by reference herein.

BACKGROUND

1. Field of the Invention

The invention generally relates to medical devices, in particular, to infusion pumps configured to deliver medication (in a fluid form) to subjects (such as patients) and, more specifically, to infusion pumps with an RFID-controlled authentication system.

2. Description of Related Art

In the field of medical care, medical pump devices, also referred to as infusion pumps, are used to deliver fluids to patients. Such infusion pumps permit the controlled delivery of fluids to a patient with high accuracy. They also allow flexible delivery schedules.

Because modern infusion pumps provide a broad variety of delivery schemes and schedules, these pumps have a large number of configuration and setting options, which makes the operation of a given infusion pump involved and/or difficult for an operator. The preparation of the user to the infusion pump operation routinely includes securing access rights to the function of an infusion pump depending on the qualifications and training of the user.

One example of such infusion pump is disclosed in EP 1237590. Here, the operation of the pump requires that a bar code be scanned before configuring the infusion pump to identify the user. The disadvantage of this example is that centralized administration of user rights is not possible, as identifiers of these rights are stored locally in or at the infusion pump.

WO 2009/124134 discloses an infusion pump that is connected via a network to a server, and that is configured to retrieve the configuration and user information from the server.

U.S. Pat. No. 7,743,975 B2 discloses an infusion pump including an optical imaging and an RFID reading modules connected through a host interface.

US 2016/0228633 A1 discloses an infusion pump in which an RFID sensor is used. In operation, the RFID sensor can contain identification information about the owner of a RFID tag. This information is used to identify the individual who is interacting with the pump and provides additional authentication security for the pump operation to ensure that, for example, patients, family members, and friends do not modify pump settings without proper authorization to do so.

SUMMARY

The embodiments provide an infusion pump system and an RFID reader for user identification in an infusion pump system.

In one embodiment, an infusion pump system includes an infusion pump and an RFID reader. The infusion pump may further include a liquid pump unit, a display, a keyboard, a controller and a communication interface. The controller may be configured as a microcontroller, and, in operation, it controls the performance of the infusion pump, and while optionally reading data from the keyboard, sending data to the display, and communicates with the via the communication interface with external devices.

The infusion pump may be operated and/or configured by an operator, (a user, such as a doctor or a nurse, for example) by entering relevant parameters via the keyboard or a control unit. The entered information/parameters/data representing patient data and/or operating parameters like dosage and/or configuration parameters and further user information are displayed on a display of the system, which may alternatively or in addition have a touch screen to support entry of data. Based on this configuration of user information and additional information that may already be stored or pre-configured in the infusion pump's memory, the fluidic pump is caused to form or generate a flow of fluid (for example, a chemical composition representing a medication) towards a target location in need of such fluid through an attached tube, according to the configuration.

User authentication information is provided by the RFID (radio-frequency identification) reader. To provide such user authentication information, it is required that the users have an RFID device such as a transponder, which may be integrated into a chip card, for example an employee badge. This RFID device must be brought into proximity to the RFID reader close enough to allow for a communication between the two. The RFID reader will then query the RFID device and request user identification. The communication (or portions) thereof between the RFID reader and the RFID device may be appropriately encrypted to increase security. After the user identification parameter(s) or data (i.e., user ID) has been received by the RFID reader, the RFID reader has to verify this user identification information and the RFID reader may further retrieve detailed user rights to access the infusion pump (referred to as the user access rights).

In at least one implementation, the RFID reader may be equipped with a cache, which is a tangible non-transitory memory (memory storage) configured to store known users (user identification parameter(s)) and preferably the corresponding user access rights as well. The stored information may include a preconfigured user selection and/or the cache may include information representing a certain number of previously identified users. If the RFID reader determines that the user identification (user ID) retrieved from the RFID device is stored in its cache, the RFID reader may proceed in its operation by checking whether the cache information is still valid or outdated. For this purpose, the memory of the RFID reader may be configured to store user identifications and associated user-related information together with an expiration date/time and/or access counter. If the cache information has expired or a certain number of accesses is reached, or if there is no information related to the user identification available in the cache for example, or if the information related to the user identification that is available in the cache is not sufficient for the purposes of access of the system, the RFID reader builds up/establishes a connection to a server that may have an appropriate data base and that provides the required information. In an embodiment, the number of cached user identification(s)—representing user access(es) to the system—may be limited to a predetermined number (for example, to 30). In an embodiment, the cache may provide preconfigured data, for example administrator rights, the purpose of which may be to provide access for maintenance or emergency configuration of the infusion pump without having access to a server. Accordingly, in one embodiment the system is configured such that the RFID reader requests user identification (and/or the user-related information) from the memory of the RFID device instead of querying the user-related information from a server. In one specific case, the RFID reader requests and receives the user-related information from the tangible memory of the RFID device and does not query the server.

In one embodiment, to limit access time to a short (pre-defined) period of time and to maintain high level of data security, only a local area communication is established between the RFID reader and the network. Such local area communication may be configured to take a form of communication from the RFID reader to an access point (which may be a WIFI access point, a Bluetooth access point, a Bluetooth low energy access point, or any other suitable access point) that is local to the locale (residence, neighborhood) where the RFID reader and the infusion pump are used. An alternative may be to build up the connection via a local personal computer providing a network or communication interface and preferably equipped with a Bluetooth or Bluetooth low energy interface. For communication with the server, the computer and/or the access point are appropriately connected to a network (which may further be connected to the server).

In an alternative embodiment, the RFID reader may access the server via a long range wide area network (LORA), which may be configured as a 5G network instead of being configured as the local communication described above.

Therefore, the RFID reader communication device may be a long range wide area network (LORA) device.

After the RFID reader has verified the user and/or obtained user information either from its internal cache or from a server, it proceeds to provide an access signal (which may further include detailed user authentication information) to the infusion pump. On the other hand, in the situation when no user verification is possible (either because there is no network access, or the server is not available, or if no sufficient user information is available), the RFID reader generates a signal representing an error message. Such an error message signal may be sent to the infusion pump, to the network server, to any other network device, or may simply be indicated by a visually perceivable indicator (for example, a flashing LED) or another indicator (such as an indicator producing an audible signal, for example) at the RFID reader.

In one implementation, the RFID reader may be configured to write back information to (to record or otherwise store such information at) the RFID device. In one non-limiting example, such information may be logging information related to and/or representing the time of access to the infusion pump and/or settings and/or parameters of the infusion pump.

In a related embodiment, the RFID reader is configured to not only provide user information to the infusion pump but also to provide configuration information and/or treatment information to the infusion pump. Such information may be a combination of treatment information associated with a specific infusion pump.

In one implementation, the communication interface of the RFID reader is configured to support a personal area network (PAN) such as e Bluetooth and/or a local area network (LAN) such as IEEE 802.11. In a preferred embodiment, the RFID reader only has a Bluetooth, and preferably only a Bluetooth low energy (BLE) interface. This specific arrangement is judiciously chosen to ensure long-time operation (on the time scale of several weeks or months) of the RFID reader even in the case when the RFID reader draws its energy from the batteries. Furthermore, this specific arrangement ensures the operation with enhanced security, because the radio signal in most cases cannot be received outside the specified locale (in the case of clinical applications—outside of the hospital). The Bluetooth low energy interface may then be used to communicate with the infusion pump and to communicate with the server either via a personal computer or an access point within the limited locally-defined space.

In a specific implementation, the embodiments configured to allow the use of the same RFID device that is used for access control like door access, in a hospital. The skilled artisan will readily appreciate that if and when there is a need to replace the RFID devices in a hospital with a new system (for example, the one with higher security) no exchange of the respectively-corresponding expensive infusion pumps is required. Instead, only the RFID readers may be exchanged or updated. In many cases, even this exchange of RFID readers may be unnecessary—in particular, when universal RFID readers (capable of being paired with a large number of RFID devices) is used.

In a related embodiment, the infusion pump may be operated and/or configured and/or switched on or off only after receiving user access information from the RFID reader and only according to properties or mode of operation assigned to the specific user or user group (as represented by the user access information). Furthermore, the access may be logged/recorded by the infusion pump, the RFID reader, or the server.

Preferably, the RFID reader has a housing separate from the infusion pump. It may also be possible to attach the RFID reader to the housing of the infusion pump, for example by means of an USB connector. In a related implementation, the RFID reader may be integrated into the housing of the infusion pump.

In one embodiment, the power supply to the RFID reader may be provided by the infusion pump, for example via a wire-based interface, when the RFID reader communication device of the RFID reader includes a wire-based interface such as USB to communicate with the infusion pump and to provide an operational flexibility to retrofit even older infusion pumps with RFID user authentication capability (because the RFID reader creates the network connection for authentication instead of the infusion pump).

In some embodiments, the infusion pump does not receive the user authentication information directly from a server. Instead, such information is forwarded via the RFID reader. In any case, however, the infusion pump may get additional information from the server.

In a related embodiment, the infusion pump may be equipped with an emergency override switch or an emergency code, which is configured to enable user's access to the infusion pump without proper authentication by the RFID reader. Depending on the specifics of the particular implementation, such emergency override switch may be protected by a key, may be a key switch, or may at least have a security cover that has to be removed before operating the emergency override switch. The cover, in turn, may have a security seal. Furthermore, the infusion pump may be complemented with appropriately-structured electronic circuitry to generate an alarm (e.g. an audible alarm or an alarm over a network) if and when the emergency override switch has been operated.

A further embodiment relates to a method of user authentication with an infusion pump.

A person of skill in the art will immediately recognize that the disclosed embodiment(s) are not only be applicable for use with an infusion pump, but also for use with another medical device configured to operate in a hospital environment (such as, for example, a pump for intravenous administration of medication (an IV pump_, an X-ray machine, a magnetic resonance imaging (MRI) system, PCs and even for a drug-cabinet access).

A related embodiment may be implemented to include RFID readers for use with phone systems or phones.

The professional trends dictate that in many companies—and especially in professional spaces occupied by lots of people—there be no longer fixed, assigned desks: Every employee is free to decide where to be and where to sit on his own. This freedom of choice causes the employee to use the telephone apparatus located at the desk at which the employee decides to sit at a given time. The employee can then establish a correspondence with (identify himself to) this particular phone apparatus. Today, such identification is implemented with the use of a PIN. However, to save time and for more convenience, this could also be effectuated with the use of an embodiment of the invention including an RFID card (if there is any), or even with a mobile phone (via NFC or BLE), in case the company uses mobile credentials or any other identification method. Then, the whole telephone is set/configured according to the last set of data representative of the employee, thereby saving time and increasing the efficiency of operation of the company.

The use of this proposed approach is especially beneficial in the hospital environments, where the use of the mobile phones might be banned due to interference risks and even cable-less telephones are not allowed. With the concept of simply "presenting" a card to any telephonic apparatus to establish a one-to-one correspondence between the apparatus and the use and to make the user "own" the telephonic apparatus for the prescribed time with his favorite setting, a doctor or nurse or another clinician can work anywhere and everywhere within the hospital without interruptions and with full confidence Accordingly, one embodiment provides an IP telephone apparatus or system equipped with an RFID reader (or other options of authentication, as already mentioned above for the IV pump). Once the employee authenticates himself to the phone, the employee's ID is send to a central server. This server has an active directory, in which the employee's ID (for example, an ID number) and the corresponding employee name are matched. Then, all the settings and telephone book entries are pushed/uploaded to the phone. As a result, the user always deals/works with/operates the "same" phone system in front of him, with the system including the chosen (at the moment) telephonic apparatus and the settings and telephone book entries of the given user.

In yet another related embodiment, an RFID reader is connected to the computer (such as PC, for example). Here, during the operation of the system, for log-on to the PC, the user needs to identify with his ID card (or other available options). However, many desktop telephone apparatus are already equipped with a BLE (Bluetooth Low Energy) functionality or sub-system. The RFID reader of the embodiment of the invention is also equipped with a BLE functionality. Therefore, the telephone apparatus in this case doesn't necessarily require its own RFID reader as described above. It is sufficient, for other purposes of sustainable operation, if the ID from the reader is sent via the BLE to the telephone apparatus, too, thereby initiating/starting the whole process described above.

BRIEF DESCRIPTION OF THE DRAWINGS

In the following, embodiments of the invention are described by way of examples, without limitations of the general inventive concept, and with reference to the drawings, of which.

Embodiments of the invention may be modified and take alternative forms. Specific embodiments are discussed below based on non-limiting examples. It should be understood, however, that the specific drawings and related portions of the disclosure are not intended to limit the scope of the invention to any particular disclosed form or implementation, but to the contrary is intended to cover all modifications, equivalents and alternatives g within the spirit and scope of the invention as defined by the appended claims.

DETAILED DESCRIPTION

Figure 1:
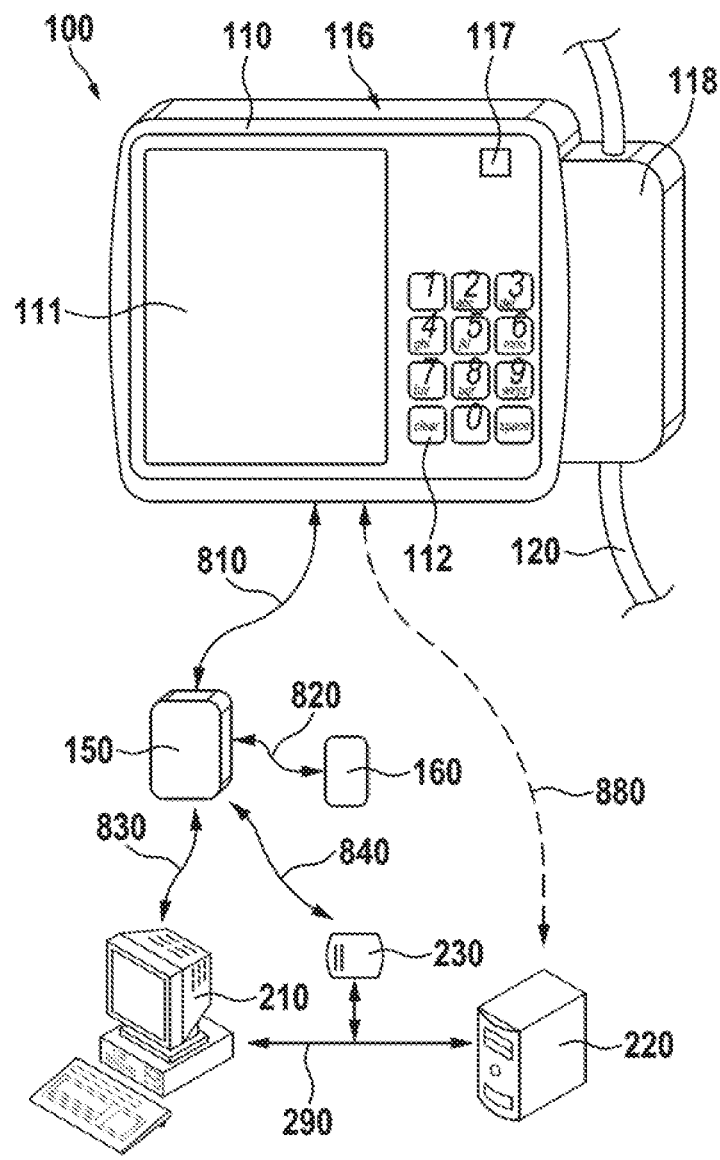
FIG. 1 is an illustration of an infusion pump system.

FIG. 1 illustrates an infusion pump system 100. An infusion pump unit or device 110 of the system 100 includes at least a controller 116, a display device 111, a keyboard (or another input control unit) 112, and a fluidic pump 118 (for example, the pump configured to pump liquid or gas). The controller 116 may, in a specific implementation, comprise an optionally-programmable micro-processor with non-transitory memory and, further, auxiliary devices that may be required to control the operation of the infusion pump. In operation, the fluidic pump 118 moves fluid (for example, liquid or gas, depending on the specific use) through a fluidic channel 120 (in one case configured as a tubular element or a tube, for example) to a target location. The infusion pump device 110 is further equipped with at least one communication interface 117 (which may be a Bluetooth, WIFI, or other communication or network interface, for example USB, depending of the specific implementation).

The infusion pump system 100 additionally includes at least one RFID reader 150. The RFID reader 150 has means to communicate 820 with an RFID device or transponder 160. The RFID reader 150 queries, in operation of the system 100, a user identification from the transponder 160 and forwards 810 access rights to the infusion pump device 110. The RFID reader 150 has further means to communicate 830 with a personal computer 210 and/or communicate 840 with an access point 230. The personal computer 210 only serves as a gateway to a network 290, to which a server 220 is connected. The access point 230 is also configured to provide access to the network 290, and therefore to the server 220. After receiving the user information from the transponder 160, the RFID reader 150 communicates either via the personal computer 210 or via the access point 230 with the server 220, and submits a request for detailed access information based on the user identification. Finally, this access information containing user access rights and other optional information is forwarded to the infusion pump device 110.

Alternatively or in addition, the RFID reader device 150 may be configured to also provide a cache for storing access rights based on user identifications (to make it unnecessary to build up or establish communication to the server 220 in each and every instance of operation).

There may also be present an operational connection 880 between the infusion pump device 110 and the server 220, for example to receive and/or provide patient information or information representative of a treatment plan. These type of information and, accordingly, the operational configuration of the connection 880 are made independent of the user authentication, as disclosed above.

Figure 2:
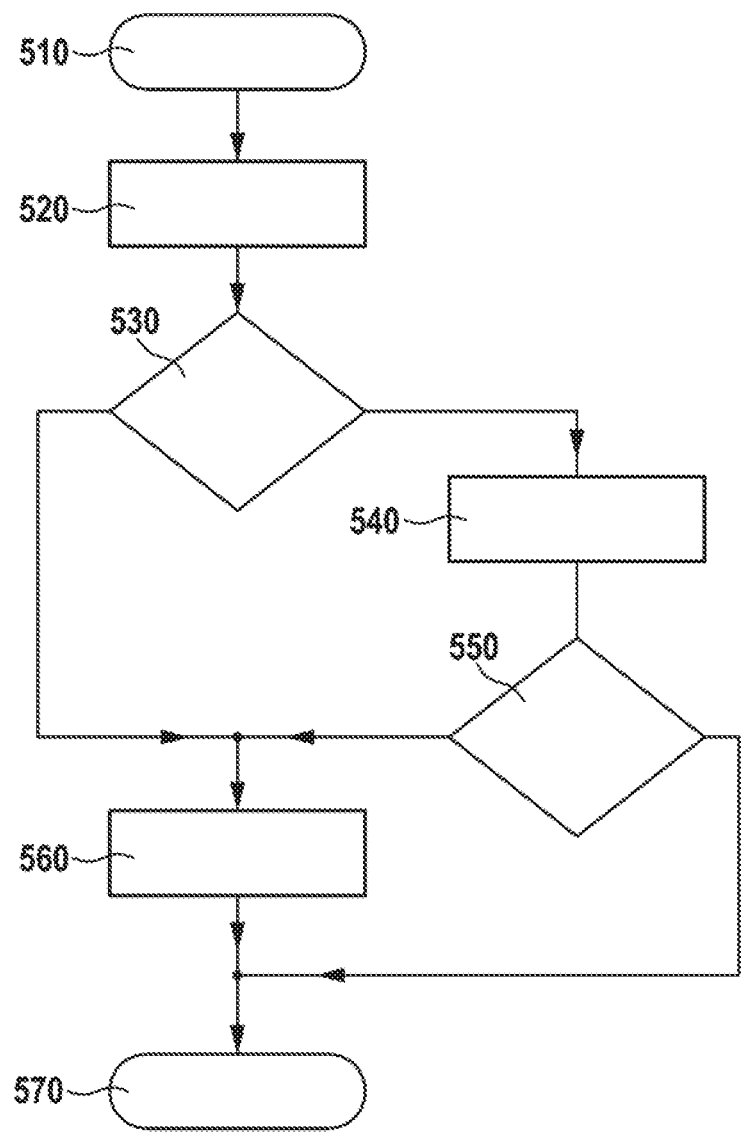
FIG. 2 is a diagram illustrating an authentication process.

FIG. 2 shows a flow chart or diagram representing at least a portion of the process of authenticating a user. The process starts at 510. The transponder or RFID device 160 identifies itself and/or provides a user identification at the RFID reader 150 in step 520. The user identification process may be configured to identify a single person, a group of multiple persons (users), or both. The transmission of identification data may be secured by encryption of the exchanged data. After this step 520 of identification, the RFID reader 150 has received a single user ID or user group ID from the RFID device 160. In the next step 530, the RFID reader 150 performs a determination (checks) whether access information associated with this received user ID is available and valid in the local RFID reader's memory. If the access information is either outdated or not available, the updated information is requested from the server 220 in step 540. In the next step 550, the response from the server 220 is analyzed: in the case when no response or no valid response is obtained or when the server indicates that the user has no access rights, the process is terminated in 570. Before the termination, an error message may be generated.

However, if valid access data are provided by the server or, alternatively, if valid data are present in the cache, the user access information is transmitted directly to the infusion pump device 110 in step 560. The infusion pump device 110 is configured to provide access rights and/or access options and/or configuration options to the user, based on the so-transmitted access information. In the next step 570, the process is terminated.

Figure 3:
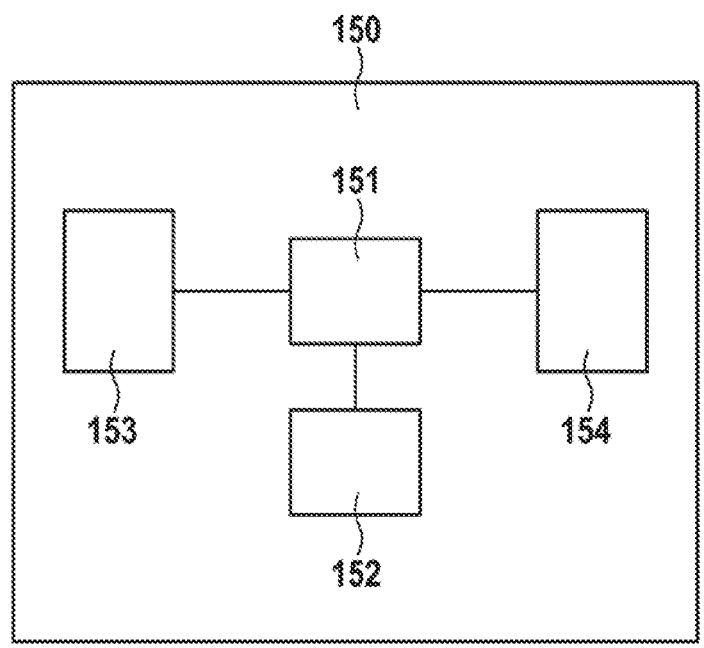
FIG. 3 is a schematic depiction of an RFID reader.

In FIG. 3, a schematic diagram of the RFID reader 150 is shown. The reader 150 includes a central processing unit 151 and a tangible memory 152. Furthermore, the RFID reader 150 comprises an RFID management device 153, which includes at least an RFID antenna, signal processing means and/or communication means (configured, for example, to transmit energy to and to communicate with the RFID device), and optional encryption means. To communicate with a network server and/or the infusion pump 110, at least one RFID reader communication device 154 is also provided. This RFID reader communication device 154 preferably is a Bluetooth-based device, but may also be a WIFI device. Preferably, it is a Bluetooth low energy device, in which case the RFID reader 150 is practically-enabled to be operated with batteries for a longer period of time (for example, for a couple of weeks of months). In the specific case when the infusion pump 110 has no wireless network interface, the RFID reader communication device 154 may also be configured to include a wired network adapter (such as, for example, an USB adapter) for communication with the infusion pump 110.

It will be appreciated by those skilled in the art having the benefit of this disclosure that specific implementations of this invention provide infusion pump systems and methods to operate infusion pump systems. Further modifications and alternative embodiments of remain within the scope of the invention.

For example, embodiments of the invention provide an infusion pump system that includes an infusion pump device and a RFID reader configured to communicate with an RFID device. The infusion pump device includes a controller, a communication interface, and a fluidic pump; while the RFID reader device includes a microcontroller, a tangible memory storage, a RFID manager circuitry and a RFID reader communication device. Here, the RFID manager circuitry is appropriately configured to receive a user identification parameter from an RFID device, and the RFID reader communication device of the RFID reader device is configured to communicate with at least one of a local personal computer and an access point connected to a network (to query user-related information based on a user identification from a server over the network) and to communicate with a communication interface of the infusion pump device to forward the user-related information to the infusion pump device. In one implementation, the memory storage of the RFID reader device is configured to store user identifications and the user-related information associated with the user identifications, and the RFID reader device is configured to retrieve the user-related information from the memory instead of querying the user-related information from the server. In a related case, the memory storage of the RFID reader device is configured to store user identifications and the user-related information associated with the user identifications together with at least one of an expiration date, expiration time, and an access counter, while the RFID reader device is configured to retrieve the user-related information from the memory storage instead of querying the user-related information from the server only if information contained in a cache of the RFID reader device has not expired and a predetermined number of user accesses to the system has not been reached. The RFID reader communication device of the RFID reader device may include a Bluetooth device or a Bluetooth Low Energy device and/or the RFID reader communication device may include a long range wide area network (LORA) device. In a specific case, the infusion pump device comprises at least one of a keyboard, a touchscreen, and an input control unit (here, the infusion pump device is configured to accept a user input only after the user-related information has been received by the infusion pump device and according to the user-related information).

Various disclosed elements, components, and materials may be appropriately substituted and certain features of the invention may be utilized independently without departing from the spirit and scope of the invention as described in the following claims.

LIST OF REFERENCE NUMERALS

100 Infusion pump system
110 infusion pump device
111 display
112 keyboard/an input control unit
116 controller
117 communication interface
118 fluidic pump
120 tube/tubular element
150 RFID reader device or circuitry
151 microcontroller
152 memory
153 RFID manager (circuitry)
154 RFID reader communication device or circuitry
160 transponder
210 personal computer
220 server
230 access point
290 network
510-570 steps of authentication 810 operational configuration establishing communication between the infusion pump device and the RFID reader
820 operational configuration establishing communication between the
RFID reader and the transponder
830 operational configuration establishing communication between the RFID reader and the personal computer
840 operational configuration establishing communication between the RFID reader and the access point
880 operational configuration establishing communication between the infusion pump device and the server

The invention claimed is:

1. A medical system comprising a medical device, configured to operate in response to an input provided to the medical device by a clinician in a clinical setting, and a radio-frequency identification (RFID) reader,
the medical device further comprising at least a controller and a communication interface,
the RFID reader further comprising at least a microcontroller, a tangible memory, an RFID manager device, and an RFID reader communication device,
wherein the tangible memory of the RFID reader is configured to store user identifications and the user-related information associated with the user identifications together with at least one of an expiration date, expiration time, and an access counter,
the RFID manager device being configured to receive a user identification from the RFID reader communication device, and
the RFID reader communication device is configured to retrieve the user-related information from the memory but only if information contained in the tangible memory has not expired and a predetermined number of user accesses of the medical system has not been reached, and
to establish operable connection with a communication interface of the medical device to forward the user-related information to the medical device.

2. The medical system according to claim 1, wherein the RFID reader communication device of the RFID reader comprises a Bluetooth device.

3. The medical system according to claim 1, wherein the RFID reader communication device of the RFID reader comprises a Bluetooth Low Energy device.

4. The medical system according to claim 1, wherein the RFID reader communication device comprises a long range wide area network (LORA) device.

5. The medical system according to claim 1, wherein the medical device is configured as one of i) a device transferring, in operation, a fluid to a target location; ii) an X-ray machine; and iii) a magnetic resonance imaging (MRI) system.

6. The medical system according to claim 5, wherein at least one of the following conditions is satisfied:
(i) the medical device comprises at least one of a keyboard, a touchscreen, an input control unit, and the medical device is configured to accept the input only after the user-related information has been received by the medical device and according to the user-related information,
ii) the medical system includes one of an X-ray imaging system and the magnetic resonance imaging (MRI) system; and
iii) the fluid includes a chemical composition representing a medication while the target location includes a tissue in need of said medication.

7. The medical system according to claim 1, wherein the medical device includes a fluidic pump configured to operate in a mode defined by the input received at the controller of the medical device after the user-related information has been recognized by the medical system as describing a user from a number of pre-approved users.

8. The medical system according to claim 1, wherein the medical device includes the infusion pump device, the infusion pump device containing a fluidic pump and at least one of keyboard and a touchscreen, wherein the infusion pump device is configured to accept the input only after the user-related information has been received by the infusion pump device.

9. A method of authenticating a user with a medical system comprising
a medical device, and
a radio-frequency identification (RFID) reader that includes a tangible memory and an RFID reader communication device, wherein the tangible memory is configured to store (i) user identifications and the user-related information associated with the user identifications and (ii) access counter information representing a current number of user accesses to the medical system,
the method comprising the steps of:
retrieving the user-related information from the tangible memory with the RFID reader communication device only if the user-related information contained in the tangible memory has not expired and the current number of user accesses to the medical system has not reached a predetermined number of user accesses to the medical system,
and
transmitting a signal containing said user-related information with the use of the RFID reader communication device to a communication interface of an infusion pump of the medical device.

10. The method according to claim 9, wherein the medical device is configured to transfer a fluid to a target location.

11. The method according to claim 9, further comprising accepting a user input from the user at the medical device, said user input causing a change of an operational status of the medical device.

* * * * *